US006764509B2

(12) United States Patent
Chinn et al.

(10) Patent No.: US 6,764,509 B2
(45) Date of Patent: Jul. 20, 2004

(54) PROSTHETIC HEART VALVE WITH SURFACE MODIFICATION

(75) Inventors: Joseph Andrew Chinn, Austin, TX (US); Jack R. Frautschi, Athens, TX (US); Richard E. Phillips, Jr., San Marcos, TX (US)

(73) Assignee: Carbomedics Inc., Austin, TX (US)

( * ) Notice: Subject to any disclaimer, the term of this patent is extended or adjusted under 35 U.S.C. 154(b) by 95 days.

(21) Appl. No.: 09/746,979

(22) Filed: Dec. 21, 2000

(65) Prior Publication Data

US 2001/0025196 A1 Sep. 27, 2001

Related U.S. Application Data

(63) Continuation-in-part of application No. 09/040,914, filed on Mar. 18, 1998, now Pat. No. 6,702,851, which is a continuation-in-part of application No. 08/711,431, filed on Sep. 6, 1996, now abandoned.

(51) Int. Cl.[7] ................................................. A61F 2/24
(52) U.S. Cl. ..................................................... 623/2.12
(58) Field of Search ............................... 623/11.11, 2.1, 623/2.12, 2.42, 23.76, 23.71, 23.72, 23.58, 23.59

(56) References Cited

U.S. PATENT DOCUMENTS

| 3,954,583 A | | 5/1976 | Lednicer et al. ............ 204/158 |
| 4,116,898 A | * | 9/1978 | Dudley et al. ............ 424/78.27 |
| 4,363,142 A | | 12/1982 | Meyer ............................. 3/1.5 |
| 4,364,127 A | | 12/1982 | Pierce et al. ...................... 3/1.5 |
| 4,613,517 A | * | 9/1986 | Williams et al. ............ 427/2.24 |
| 4,751,120 A | * | 6/1988 | Yazaki et al. ............... 428/36.7 |
| 4,979,959 A | | 12/1990 | Guire ............................ 623/66 |
| 5,002,582 A | | 3/1991 | Guire et al. .................... 623/66 |
| 5,017,670 A | | 5/1991 | Frautschi et al. ............. 527/313 |
| 5,019,393 A | | 5/1991 | Ito et al. ....................... 424/423 |
| 5,098,960 A | | 3/1992 | Frautschi ................... 525/359.3 |
| 5,098,977 A | | 3/1992 | Frautschi et al. ............. 527/313 |
| 5,112,615 A | | 5/1992 | Ito et al. ....................... 424/426 |
| 5,126,140 A | | 6/1992 | Ito et al. ....................... 424/423 |
| 5,167,960 A | | 12/1992 | Ito et al. ....................... 424/423 |
| 5,263,992 A | | 11/1993 | Guire ............................ 623/66 |
| 5,509,932 A | | 4/1996 | Keogh et al. .................. 623/11 |
| 5,554,184 A | | 9/1996 | Machiraju ....................... 623/2 |

OTHER PUBLICATIONS

Rittenhouse, Edward A., MD; Mohri, Hitoshi, MD, Dr. Med. Sci; Reichenbach, Dennis D., MD; and Merendino, K. Alvin, MD, PhD; *Heparin–Bound Aminoethylcellulose as in Antithrombogenic Surface*, Arch Surg/vol. 105, Nov. 1972, pp. 752–755.

(List continued on next page.)

*Primary Examiner*—David J. Isabella
(74) *Attorney, Agent, or Firm*—Williams, Morgan & Amerson, P.C.

(57) ABSTRACT

Biocompatible prostheses, specifically, biocompatible heart valves, are described having incorporated therein an effective amount of coating applied thereto to render the valve resistant to in vivo pathologic thrombus formation and in vivo pathologic mineralization. Preferably, the coating is derived from a precursor having the formula:

X—Y—Z wherein X is a chemically reactive group capable, upon activation, of bonding to the surface of the heart valve; Y is either null or a relatively inert skeletal moiety resistant to cleavage in aqueous physiological fluids; and Z is a functionally active moiety or a biocompatible agent.

3 Claims, 7 Drawing Sheets

(7 of 7 Drawing Sheet(s) Filed in Color)

HP-100/³H-FA
Fatty Acid Modified SR

JFV66 (157d)  JFV67 (156d)  JFV69 (151d)

High performance silicone rubber valves, surface modified with FA-1, retrieved after 5 month ovine mitral implant.

OTHER PUBLICATIONS

Ishihara, Tokuhiro, MD; Ferrans, Victor J., MD, PhD; Jones, Michael, MD; Cabin, Henry S., MD; and Roberts, William C., MD; *Calcific Deposits Developing in a Bovine Pericardial Bioprosthetic Valve 3 Days After Implantation*, Pathology and Surgery Branches, National Heart, Lung, and Blood Institutes of Health, Bethesda, Maryland 20205, Circulation 63, No. 3, 1981, pp. 718–722.

Schoen, Frederick J.; Harasaki, Hiroaki; Kim, Kookmin M.; Anderson, H. Clarke; and Levy, Robert J.; *Biomaterial–associated calcification: Pathology, mechanisms, and strategies for prevention*, J. Biomed. Mater Res.: Applied Biomaterials vol. 22 A1, 11–36 (1988), pp. 11–36.

Chinn, Joseph A.; Frautschi, Jack R.; Phillips, Richard E. Jr.; and Bianco, Richard W., *Comparison of In Vitro and In Vivo Biostability of Surface Modified Polymers as Determined by Radiolabel*; Minneapolis, Minnesota; Sep. 1995; pp. 176–181.

Frautschi, Jack R.; Chinn, Joseph A.; Phillips, Richard E. Jr.; Bianco; Richard W.; and Schoen, Frederick J.; *Surface Modification of Prototype Polymer Valves Improves Valve Performance in the Ovine Mitral Model*; 1995 Surfaces in Biomaterials Foundation, pp. 116–120.

Chinn, Joseph A.; Phillips, Richard, Jr.; and Moore, Mark; *A new Generation of Heart Valves*; Sulzer Technical Review; Apr. 1996; pp. 34–35.

\* cited by examiner

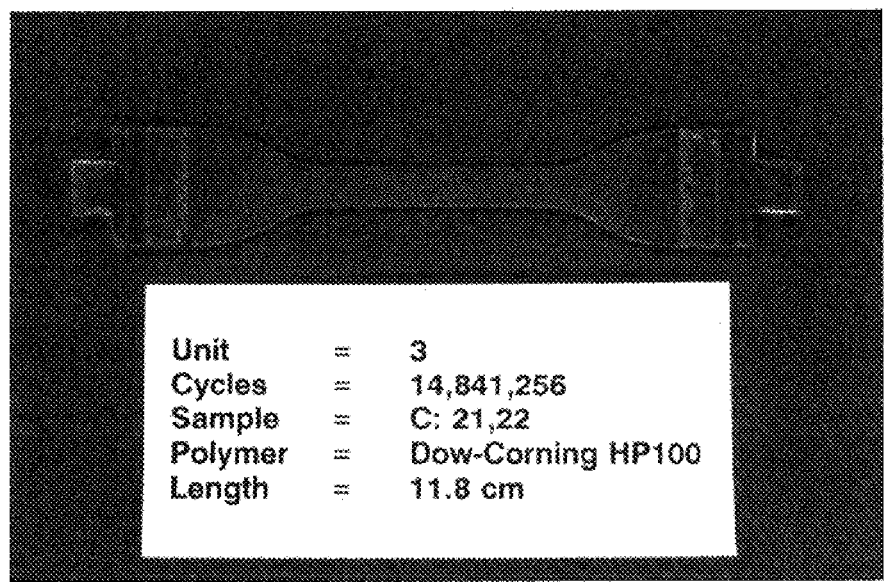
Figure 1: Photograph of HP100 sample after 12 weeks incubation under cyclic strain in calcium and phosphate supplemented, heparinized, bovine plasma.

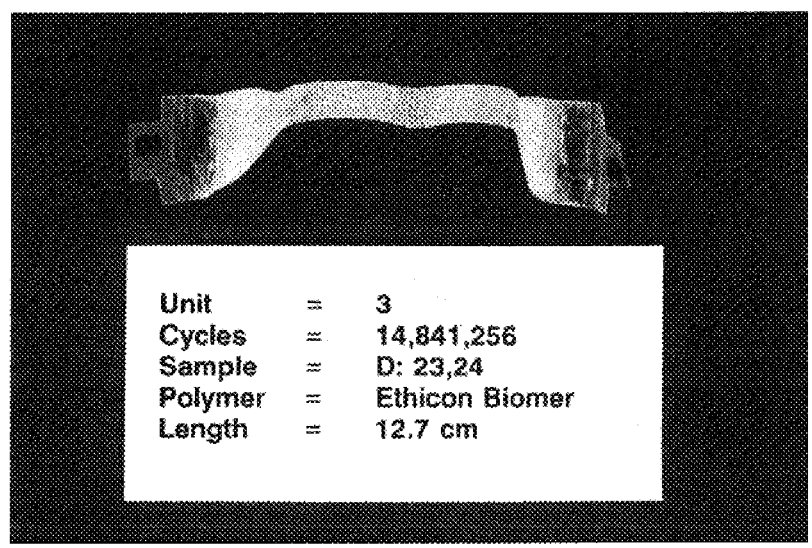
Figure 2: Photograph of Ethicon biomer sample after 12 weeks incubation under cyclic strain in calcium and phosphate supplemented, heparinized, bovine plasma.

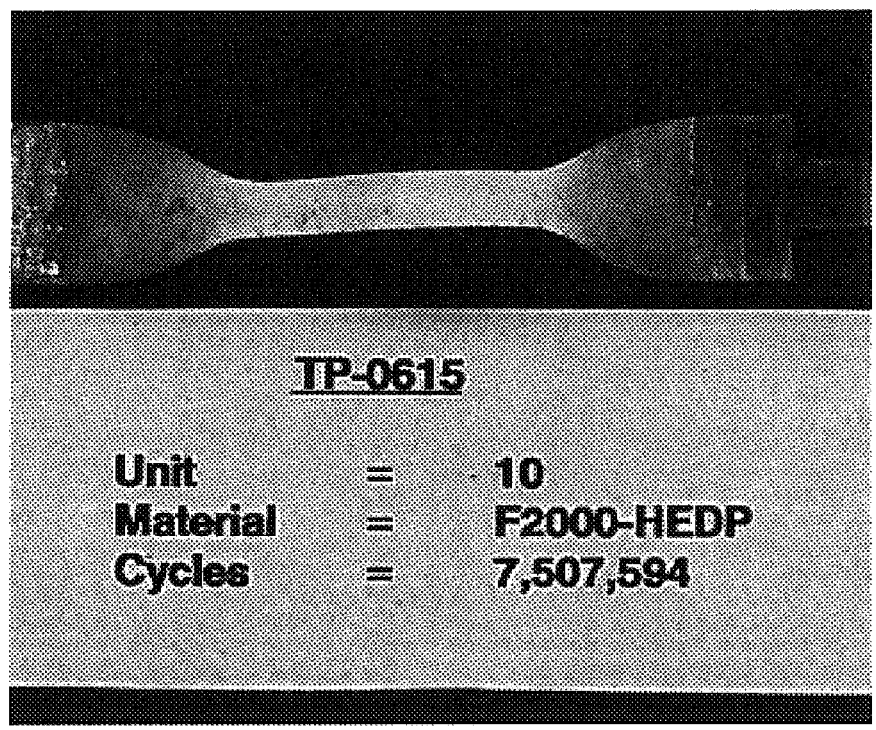
Figure 3: Photograph of F2000-HEDP after 6 weeks incubation under cyclic strain.

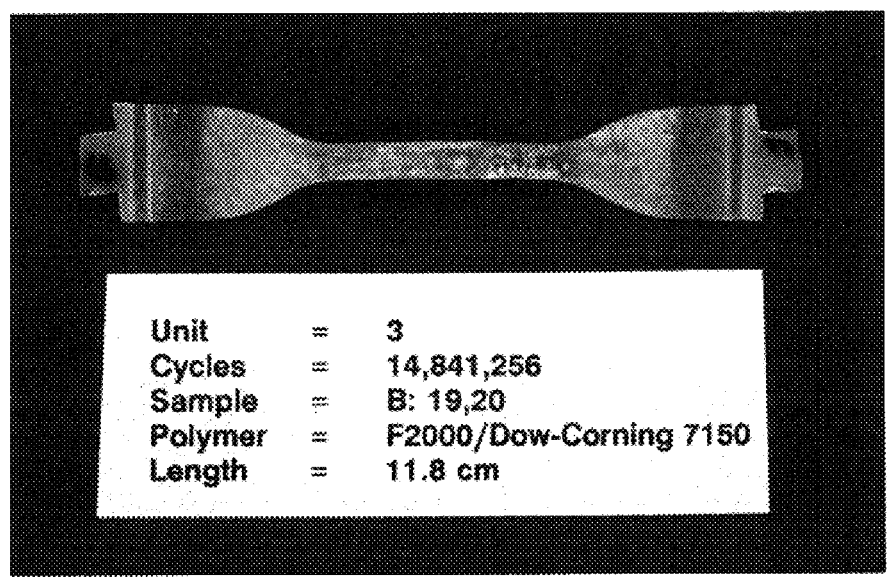
Figure 4: Photograph of F2000/Dow Corning 7150 sample after 12 weeks incubation under cyclic strain in calcium phosphate supplemented, heparinized, bovine plasma.

HP-100/ ³H-HA
Hyaluronic Acid Modified SR
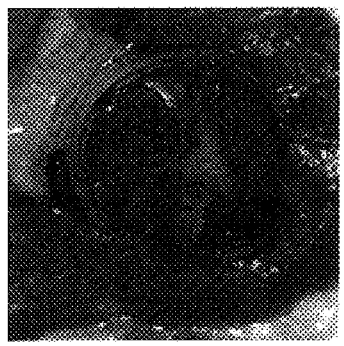
JFV61
(151d)
JFV62
(151d)
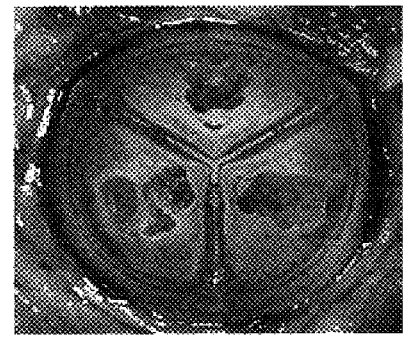
JFV64
(155d)
Figure 5: High performance silicone rubber valves surface modified with HA-1, retrieved after 5 month ovine mitral implant.

HP-100/³H-FA
Fatty Acid Modified SR
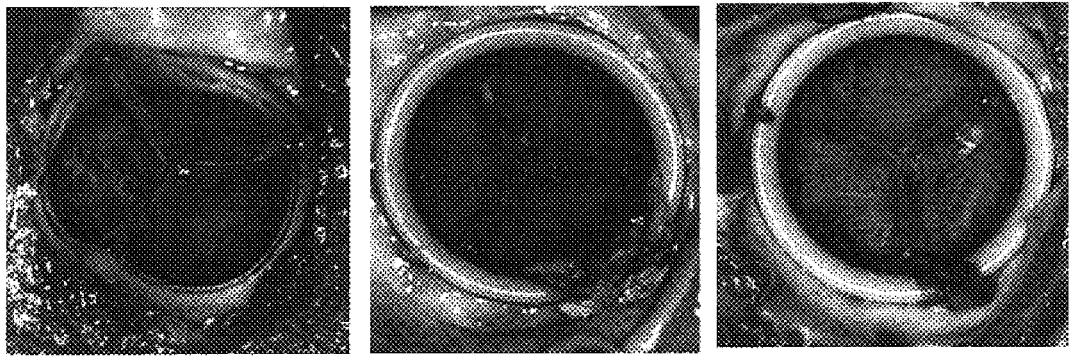
JFV66  JFV67  JFV69
(157d)  (156d)  (151d)
Figure 6: High performance silicone rubber valves, surface modified with FA-1, retrieved after 5 month ovine mitral implant.

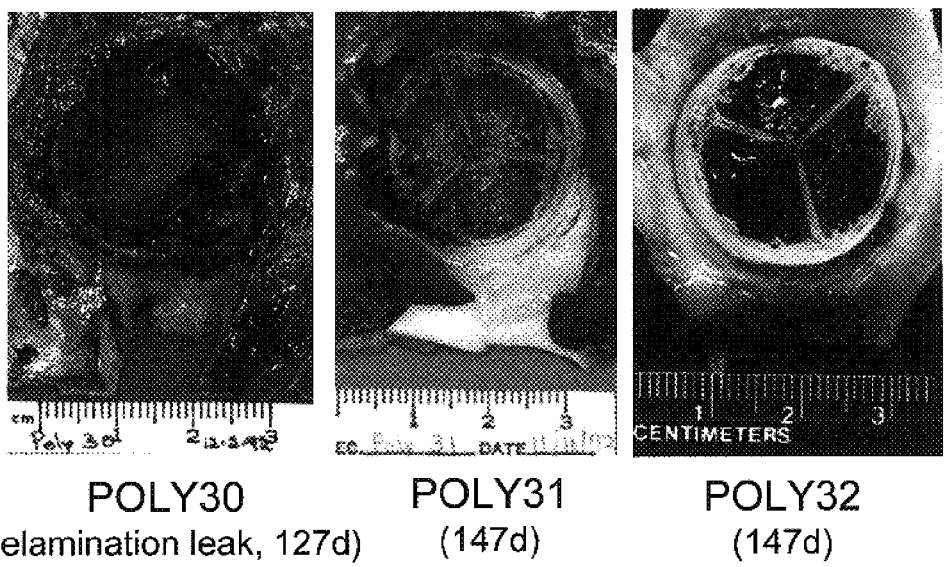
Figure 7: Photographs of high performance silicone rubber valves retrieved after 5 month ovine mitral implant.

PROSTHETIC HEART VALVE WITH SURFACE MODIFICATION

The present application is a continuation-in-part of co-pending U.S. patent application Ser. No. 09/040,914, filed Mar. 18, 1998 now U.S. Pat. No. 6,702,851, which was a continuation-in-part of U.S. patent application Ser. No. 08/711,431, filed Sep. 6, 1996, now abandoned. The entire text of each of the above-referenced disclosures is specifically incorporated by reference herein without disclaimer.

FIELD OF THE INVENTION

The present invention relates generally to the field of biocompatible prosthetic devices having increased resistance to mineralization and thrombus formation. More particularly, it concerns biocompatible heart valves comprising an effective amount of a thrombus-inhibiting and mineralization-inhibiting coating. The present invention also features a novel method for manufacturing heart valves comprising an effective amount of a thrombus-inhibiting and mineralization-inhibiting coating.

BACKGROUND OF THE INVENTION

Continuing advances in heart valve prosthesis design and techniques for implantation have improved the survival length and quality of life of patients who receive these devices. In an ongoing effort to develop a more durable and compatible heart valve prosthesis, researchers have used a variety of techniques to determine the suitability of given valve materials for a given implant application. This suitability is generally known as "biocompatibility." Researchers commonly deal with biocompatibility in terms of whether the implant material or its degradation products, if any, initiate adverse tissue responses in the host, or conversely, whether deleterious changes in the chemical, physical, or mechanical properties of the implant material are caused by the host environment. The term "hemocompatibility" refers to biocompatibility issues related with implantation in the cardiovascular system, such as any toxicity of implant materials to red blood cells or tissues contacted by the material. The vast majority of biocompatibility studies to date have involved animal models. The ultimate test for biocompatibility of a material, device, or prosthesis is human implantation.

To be clinically effective, a heart valve must endure a difficult environment, including cyclic bending stresses and high pressure spikes across the valve, for long periods of time. Prosthetic heart valves currently in clinical use are of two general varieties: mechanical or tissue. Mechanical heart valves are very durable, but their use is complicated by higher risks of thromboembolism, hemorrhage, and hemolysis. Tissue valves require no chronic anticoagulation of the patient, but often fail due to mineralization (the formation of mineral deposits, e.g. calcium phosphates) and tissue tearing. Potential alternative materials that are sufficiently durable and blood compatible for use in a prosthetic heart valve include (i) non-glutaraldehyde fixed bovine pericardial tissue, which studies in an ovine mitral model show to be mineralized to a lesser extent than glutaraldehyde-fixed tissue and (ii) synthetic polymers, such as polyurethanes, which have been reported in many different models to also show less mineralization than glutaraldehyde-fixed bovine pericardial tissue.

Mineralization, however, remains an obstacle to the clinical development of a polymer-based heart valve. Artificial heart valve bladders and pacemaker leads fabricated of polyurethane have been observed to undergo mineralization in mammalian trials. The precise mechanism for pathological mineralization of cardiovascular tissue or heart valve prostheses is not well understood. Generally, the term "pathologic mineralization" refers to deposition of minerals, typically calcium phosphate mineral salts, in association with a disease process. See Schoen et al., "Biomaterial-assisted calcification: Pathology, mechanisms, and strategies for prevention," *J. Biomed. Mater. Res.*: Applied Biomaterials, Vol. 22 A1, 11—36 (1988), incorporated herein by reference. Mineralization may be due to host factors, implant factors, or extraneous factors such as mechanical stress. Some evidence suggests calcium deposits are related to devitalized cells, especially membrane cells, where the calcium pump ($Ca^{+2}$-$Mg^{+2}$-ATPase) responsible for maintaining low intracellular calcium levels is weakened or no longer functioning. Mineralization has been observed to begin with an accumulation of calcium and phosphorous (present as hydroxyapatite and other calcium phosphates), which develops into nodules that can eventually lead to a valve failure.

A permanent implantable prosthetic polymeric heart valve was first described at least four decades ago (Akutsu, T., Dreyer, B., Kolff, W. J., *J. Appl. Physiol.* 14:1045–1048 (1959)), yet reduction of the concept to clinical practice has eluded the medical device industry, due to leaflet stiffening, tearing, thrombosis, calcification, and valve stenosis not predicted by in vitro models. Reported physical properties of materials such as polyetherurethanes exceed the requirements of cardiac valves. Biomer, a polyetherurethane urea once thought to be the ideal blood contacting material for implantable devices such as heart valves, was later reported to be prone to mineralization in the juvenile sheep model (Hilbert, S. L. et al., *J. Thorac. Cardiovasc. Surg.* 94: 419–429 (1987)), and its use as a primary component of a clinical prosthetic heart valve has not materialized. While the observed mineralization was first attributed to microscopic defects in the leaflet surface, it was later appreciated that the polyether segment of the polyurethane had the capacity to associate with calcium ions in the blood leading to mineralization of the material itself (Thoma, R. J. et al., *J. Biomat. Appl.* 3:180–206 (1988)). Reports of mineralized polyurethane blood pump bladders supported the polyurethane mineralization theory (Coleman, D. L. *Trans. Am. Soc. Artif. Intern. Organs* 27: 708–713 (1981)). However, it was not appreciated that mineralized thrombus comprised the vast majority of the calcium present upon polymer valve leaflets, and therefore, for materials not inherently calcific, inhibition of leaflet thrombosis simultaneously prevents leaflet calcification.

The location of mineralization sites on a heart valve prosthesis may be intrinsic, i.e., within the boundaries of the biomaterials of the prosthesis, or extrinsic, i.e., outside the biomaterials, though possibly attached to the valve prosthesis, e.g., within thrombus or other adherent tissue. With polymer valves, it is generally believed that both intrinsic and extrinsic mineralization must be controlled. Therefore, a biocompatible heart valve prosthesis is needed that is resistant not only to thrombus formation, but also to mineralization, particularly extrinsic mineralization, i.e., mineralization of thrombus or tissue adherent to valve leaflets.

SUMMARY OF THE INVENTION

This invention relates to biocompatible prostheses that are resistant to in vivo mineralization. More particularly, this invention relates to mineralization-resistant and thrombus-resistant heart valves comprising synthetic polymers or materials of natural origin (e.g. bovine pericardium, porcine heart valves, or homografts), having incorporated therein an effective amount of a coating to impart resistance to both mineralization and thrombus formation.

This invention is also directed to a prosthetic heart valve comprising a stent defining a blood flow path and a plurality of leaflets, each leaflet having incorporated therein an effective amount of an applied coating to render the heart valve resistant to in vivo pathologic thrombus formation and resistant to in vivo pathologic mineralization. The heart valve can comprise synthetic polymers or materials of natural origin. Preferably, the leaflets comprise silicone rubber or phosphonate modified polyetherurethane.

The coating may be applied photochemically or by other coating techniques known in the art (e.g., wet chemistry), and is preferably derived from a precursor of the formula:

wherein X is a chemically reactive group capable, upon activation, of bonding to the surface of the heart valve; Y is either null or a relatively inert skeletal moiety resistant to cleavage in aqueous physiological fluids; and Z is a functionally active moiety or a biocompatible agent. In a preferred embodiment, X is a photochemically reactive group.

This invention further provides a method for reducing mineralization and thrombus formation in a bioprosthetic heart valve after implantation in an animal. The method comprises:

contacting, prior to implantation, at least a portion of the heart valve with a coating precursor of the formula:

wherein X is a chemically reactive group capable, upon activation, of bonding to the surface of the heart valve; Y is either null or a relatively inert skeletal moiety resistant to cleavage in aqueous physiological fluids; and Z is a functionally active moiety or a biocompatible agent; and bonding the precursor to at least a portion of the heart valve, to produce a heart valve with a bonded coating, wherein the bonded coating is present in an amount effective to reduce mineralization and thrombus formation after implantation. In a preferred embodiment, X is a photochemically reactive group, and the precursor is bonded to at least the leaflets of the heart valve.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIG. 1 is a photograph of a high performance silicone rubber (available under the tradename HP100, Dow Corning, Midland, Mich.) sample after 12 wk incubation under cyclic strain in calcium- and phosphate-supplemented heparinized bovine plasma.

FIG. 2 is a photograph of a polyetherurethane urea (previously available under the tradename Biomer, Ethicon Inc., Somerville, N.J.) sample after 12 wk incubation under cyclic strain in calcium- and phosphate-supplemented heparinized bovine plasma.

FIG. 3 is a photograph of an epoxy-bisphosphonate-modified polyetherurethane (hereinafter referred to as F2000-HEDP) sample after 6 wk incubation under cyclic strain.

FIG. 4 is a photograph of a polyetherurethane/polysiliconeurethane (hereinafter referred to as F2000/Dow Corning 7150) sample after 12 wk incubation under cyclic strain in calcium- and phosphate-supplemented heparinized bovine plasma.

FIG. 5 is a photograph of silicone rubber valves that were surface modified with a photoreactive precursor having a hyaluronic acid moiety, designated as HA-1, and retrieved 5 months after implantation in the mitral position of sheep.

FIG. 6 is a photograph of silicone rubber valves that were surface modified with a photoreactive precursor having a fatty acid moiety, designated as FA-1, and retrieved 5 months after implantation in the mitral position of sheep.

FIG. 7 is a photograph of silicone rubber valves that were not surface modified, retrieved 5 months after implantation in the mitral position of sheep.

DESCRIPTION OF ILLUSTRATIVE EMBODIMENTS

In one embodiment, the present invention provides a biocompatible heart valve having improved resistance to mineralization and improved resistance to thrombus formation. The valve includes a coating of a biocompatible material that provides antimineralization and antithrombotic effects over a sustained period of time. The coating can be any material that provides antimineralization and antithrombotic effects and can be coated on the heart valve. The coating can be covalently bonded to the valve, non-covalently bonded to the valve, or both. The coating can be applied by any appropriate technique. Preferably, the coating is applied by photochemical application.

Though not to be bound by theory, it is believed that mineralization of uncoated heart valves is most commonly extrinsic mineralization that occurs at sites where thrombus has adhered to the heart valve. Observations of uncoated polymer valves showed most mineralization occurred at sites of thrombus formation. Therefore, it is believed that the coated biocompatible heart valves of this invention reduce mineralization by minimizing thrombus formation.

Desirably, the coating material and the material from which the heart valve or the leaflets thereof is constructed are both compatible with all fluids of a mammalian body, i.e., when implanted in the body of a mammal, the materials are biologically inert or interact with bodily fluids to become biologically inert, physiologically acceptable, non-toxic, and insoluble. The materials from which the heart valve is constructed are typically naturally derived or based on a synthetic biocompatible organic polymer.

Synthetic biocompatible organic polymers which can be used in the present invention include, but are not limited to, siloxane polymers, polydimethylsiloxanes, silicone rubbers, polyurethane, polyether urethane, polyetherurethane urea, polyesterurethane, polyamide, polycarbonate, polyester, polypropylene, polyethylene, polystyrene, polyvinyl chloride, polytetrafluoroethylene, polysulfone, cellulose acetate, polymethylmethacrylate, and poly(ethylene/vinylacetate). Natural materials from which the heart valve can be constructed include bovine pericardium tissue and porcine tissue, among others.

In one preferred embodiment, the heart valve is constructed from a high performance silicone rubber, such as a platinum-catalyzed silicone elastomer made from dimethylsiloxane, as is known by the tradename HP-100 (Dow Corning, Midland, Mich.; an alternate Dow Corning product code for this product is X7-4978). Other silicone rubber polymers may be used.

In another preferred embodiment, the heart valve is constructed from a modified polyetherurethane. Although preparation of an exemplary phosphonate-modified polyetherurethane, referred to herein as "F2000-HEDP," is described herein, the invention is not restricted to any particular polyetherurethane species. The base polyetherurethane (PEU F-2000) is synthesized from diphenylmethane-4,4'-diisocyanate (MDI), a 1,4-butanediol chain extender (BD), and a polytetramethylene oxide with a molecular weight of about 2000 (PTMO-2000) (available under the tradename Terethane 2000 Polyether Glycol, Dupont, Wilmington, Del.). The reactant ratio of MDI:BD:PTMO-2000 is 5:3:2, with 1.7% hydroxyl excess. The modified polyetherurethane is obtained by reacting, typically, ethanehydroxydiphosphonate (HEDP, available from Monsanto Company, St. Louis, Mo., as Dequest 2010) with a polyfunctional epoxide (such as Denacol 521, available from Nagasi Chemicals, Osaka, Japan), and then with the PEU F-2000 base polymer. (Details on the synthesis of F2000-HEDP are provided in U.S. Pat. No. 5,436,291, whose entire contents are hereby incorporated by reference herein). The ratio of HEDP to total final polymer is typically about 100 to about 400 nmol/mg.

In yet another preferred embodiment, the heart valve composite is constructed from a polyurethane. An exemplary preferred polyurethane is a polyetherurethane urea formerly available under the tradename Biomer (Ethicon Inc., Somerville, N.J.).

In a further preferred embodiment, the heart valve is constructed from a polyetherurethane/polysiliconeurethane. An exemplary preferred polyetherurethane/polysiliconeurethane may be referred to herein as "F2000/Dow Corning 7150," although other polyetherurethane/polysiliconeurethanes can be used. A typical heart valve made from F2000/Dow Corning 7150 comprises F2000 polyetherurethane, as described above, with a final coat of a polysiliconeurethane, such as formerly available as Dow Coming 7150, now available as Dow Corning X7-4074.

In still another preferred embodiment, the heart valve is constructed from a natural material, such as bovine pericardium.

The heart valve can also comprise other materials. For example, the valve can be either a stented valve or a stentless valve, although stented valves are preferred. For stented valves, the stent material is typically a hard polymer, such as high durometer polyurethane, polyacetal, or another polymer with a high degree of stiffness. However, other stent materials, for example, metals such as titanium alloy or Nitinol, can be used. In preferred embodiments, the valve has two or more leaflets, typically three. If constructed with a polymer such as silicone rubber or modified polyetherurethane, the valves are typically constructed as follows: the polymer is dissolved in a solvent, e.g. 1,1,1-trichloroethane (TCE) (for silicone rubber) or an amide such as dimethylacetamide (DMAC) or dimethylformamide (DMF) (for polyetherurethane), respectively. Other solvents may be employed without departing from the scope of the invention. Selection of suitable solvents for particular polymers is within the level of ordinary skill in the art. Typically, the polymer is dissolved to about 8–14% w/v, more preferably about 10% w/v, although this concentration can be varied as desired. After the polymer is dissolved, a stent is repeatedly dipped into the polymer solution and dried in air at about 15–25% relative humidity, preferably about 20% relative humidity. The polymer-coated stent is then placed over a leaflet mandrel, which is dipped several times into the solution and dried as above, to provide heart valve leaflets of a desired thickness. In addition to the dipping technique described herein, the valve may be formed by injection, transfer, or compression molding, thermoforming, or other techniques known in the art.

However constructed, the heart valves of the present invention are coated with organic molecules that impart resistance to in vivo mineralization and in vivo thrombus formation. Any such organic molecules can be used. In a preferred embodiment, the coating is derived from a precursor of the formula:

wherein X is a chemically reactive group capable, upon activation, of bonding to the surface of the heart valve; Y is either null or a relatively inert skeletal moiety resistant to cleavage in aqueous physiological fluids; and Z is a functionally active moiety or a biocompatible agent. More preferably, X is a photochemically reactive group. Such groups and their photochemistry are described in U.S. Pat. Nos. 4,979,959, 5,002,582, and 5,263,992, whose entire contents are incorporated by reference herein.

X may be derived from a compound selected from aryl azides, alkyl azides, acyl azides, azidoformates, sulfonylazides, phosphoryl azides, diazo compounds, diazirines, ketenes, or aromatic ketones. In a particularly preferred embodiment, X is derived from a photoreactive substituted benzyl benzoyl having structure I:

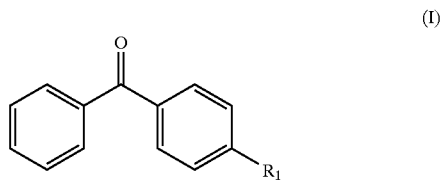

wherein R1 is a carboxyl group or a methylchloride group.

Y may be derived from a compound selected from $C_1$–$C_{10}$ alkyldiol or diamine; polyethyleneoxide (PEO); amino-substituted PEO (MW=200–1450); diamine-terminated PEO (MW=200–1450); ε-amino caproic acid (EAC); ethylene diamine (ED); or diaminopropane (DAP). In a particularly preferred embodiment, Y is derived from DAP. In another particularly preferred embodiment, Y is derived from a diamine-terminated amide, more particularly derived from the reaction product of EAC and ED.

Z may be derived from a compound selected from functionalized $C_1$–$C_{18}$ alkylene, functionalized mucopolysaccharides, functionalized polyoxyethylene, functionalized vinyl polymers, or functionalized polypeptides. By "functionalized" is meant that the compound comprises a group capable of forming a covalent bond with an alcohol group or an amine group of the compound from which Y is derived. Appropriate groups that functionalize the compounds from which Z may be derived include carboxyl, amine, or alkylhalide, as well as others apparent to one of ordinary skill in the art. In preferred embodiments, Z is derived from a compound selected from functionalized fatty acids, functionalized hyaluronic acid, functionalized polyoxyethylene, functionalized heparin, or functionalized polyvinylpyrrolidone. More preferably, Z is a fatty acid derivative or a hyaluronic acid derivative. Precursors having such Z groups together with X groups comprising photoreactive benzophenone moieties, may be referred to as photoreactive fatty acid, photoreactive hyaluronic acid, photoreactive polyoxyethylene, photoreactive heparin, or photoreactive vinylpyrrolidone, respectively.

The more preferred precursors include those having structures II or III:

fatty acid Z group) is able to bind albumin found in serum, by both polar associations between a polar moiety or moieties of the albumin and the carboxyl (—COOH) moiety of the fatty acid, and hydrophobic interactions between the alkyl chain of the fatty acid and a hydrophobic moiety or moieties of the albumin. The binding of albumin may be reversible or it may be substantially irreversible. Regardless, it is believed that an equilibrium level of albumin binding will be reached, preferably at levels sufficient to protect the prosthesis against thrombus accumulation and mineralization. It is believed that the first step of thrombosis is platelet binding to proteins via protein-specific receptors on platelets. Platelets are not known to have receptors for albumin, and therefore, sufficient levels of albumin are believed to screen the prosthesis from platelets.

A precursor of the present invention is typically prepared by a two-step process. First, the R1 moiety of the X group,

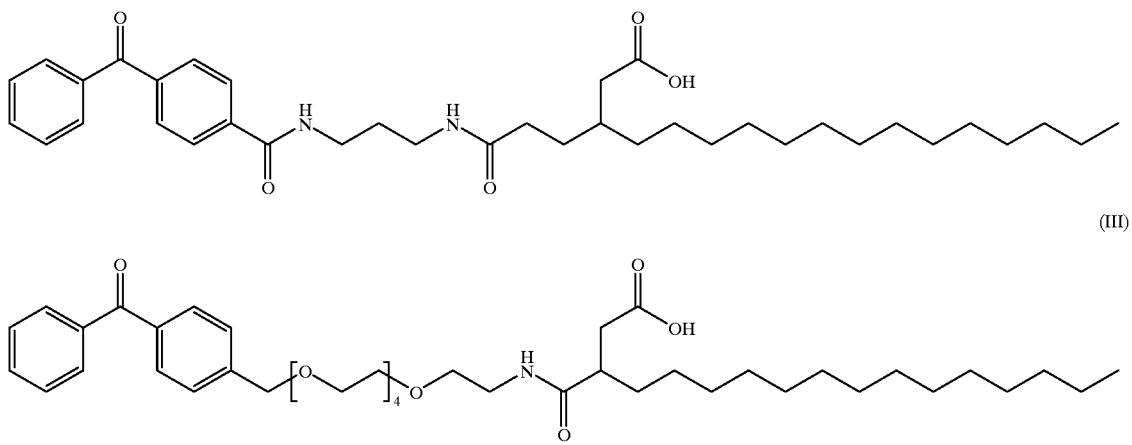

The compound of structure II may be referred to as "photoreactive fatty acid-2" or "photo FA-2." The compound of structure III may be referred to as "photoreactive fatty acid-1" or "photo FA-1."

Most preferably, the precursor has structure II, i.e., X is derived from a substituted benzyl benzoyl group, Y is derived from DAP, and Z is derived from a fatty acid. Though not to be bound by theory, it is believed that, once coated onto a surface, this molecule (or others comprising a typically a carboxyl moiety, is reacted with an appropriate moiety on the Y or Z group, such as an amino group as available when the Y group is derived from diaminopropane (DAP) to form an amide linkage. Thereafter, a reactive moiety on the Y group (such as an amino moiety on a Y group derived from DAP) is then reacted with a precursor of the Z group, for example, an alkyl anhydride, as shown by example in Equation 1.

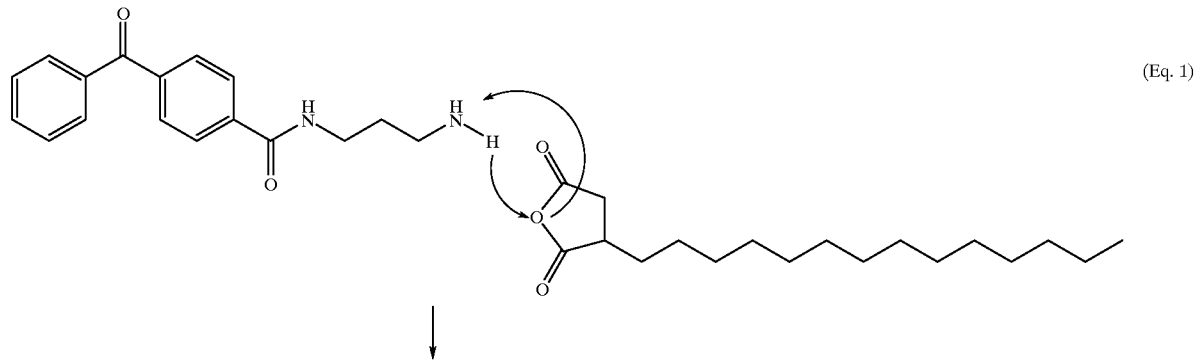

-continued

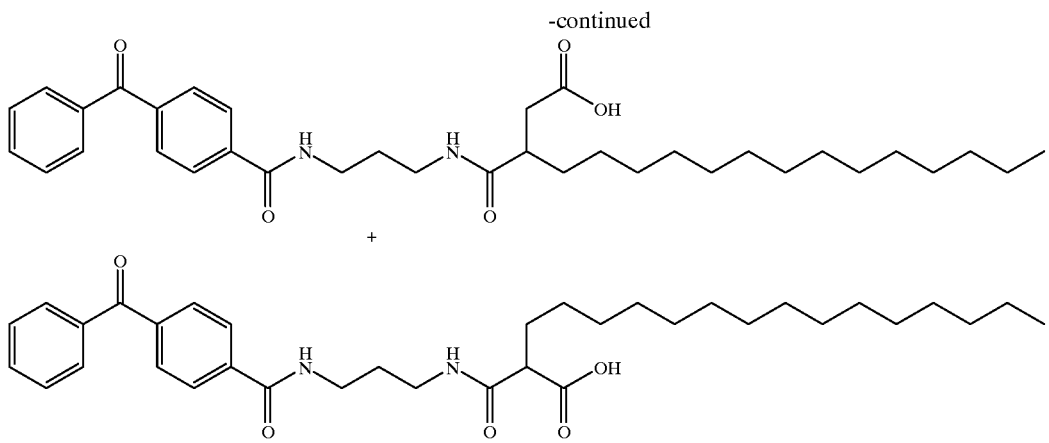

+

It is believed the two isomers of the fatty acid-containing coating precursor of Equation 1 are substantially equivalent in functionality.

Preferably, the linkage between X and Y is either an amide linkage (formed by a reaction between a carboxyl group of X and an amine group of Y) or an ether linkage (formed by a reaction between a methylchloride group of X and a hydroxyl group of Y), although other linkages are possible depending on the chemistry of the reactive groups of X and Y. Preferably, the linkage between Y and Z is an amide linkage (formed by a reaction between an amine group of Y and a carboxyl group of Z), although other linkages are possible depending on the chemistry of the reactive groups of Y and Z.

To apply the coatings of the present invention to a valve constructed as disclosed above, typically a heart valve including the leaflets is dipped one or more times into a solution comprising the coating precursor (such as about 5 mg/mL precursor with a fatty acid-derived Z group in isopropanol), followed by photolytic activation. In one typical embodiment, the heart valve is dipped into the solution for about 1 min at room temperature, slowly withdrawn from solution, air dried (preferably in air at 20% humidity or less), and illuminated for about 3 min at about 2 mW/cm$^2$ intensity in the range of 335–345 nm, using dual Dymax PC-2 light sources (peak output 365 nm). The procedure can be repeated as desired to achieve a desired thickness.

It may also be desirable to use a photoprimer, such as tetrakis(4-benzoylbenzyloxymethyl) methane (SurModics), in order to facilitate the coating of the precursor to the surface. Details on the synthesis of this compound are provided in U.S. Pat. Nos. 5,414,075 and 5,637,460, whose entire contents are hereby incorporated by reference herein.

The above materials and techniques provide the heart valve with a coating that imparts resistance to mineralization and resistance to thrombus formation. Though not to be bound by theory, it is believed the coatings are bonded to the polymer surface of the heart valve either by covalent interactions, non-covalent interactions (such as van der Waals interactions), or both.

Experimental

Surface modified heart valves comprising surface modified leaflets according to the present invention were tested using the ovine mitral model described by E. D. Irwin et al., "Long term evaluation of prosthetic mitral valves in sheep," *J. Invest. Surgery*, 6, 133–141 (1993). Briefly, juvenile sheep (30–35 kg to insure good valve size fit) were selected. The native mitral valve was excised and replaced with a heart valve of the present invention or a control. The valves were retrieved at about 150 days after implantation, fixed in 10% neutral buffered formalin, and subjected to histological evaluation. Histological sections were prepared in glycol methacrylate or paraffin and stained with hematoxylin and eosin for cellular detail, and using the von Kossa stain for calcium and phosphate as described in F. J. Schoen et al., "Calcification of bovine pericardium used in cardiac valve bioprostheses. Implications for the mechanisms of bioprosthetic tissue mineralization," *Am. J. Pathol.* 123, 134–145 (1986). The valves were also radiographed, photographed, and visually examined for the presence of thrombi and vegetations, abnormalities (such as endocarditis), leaflet condition, and valve functionality.

Upon gross examination, surface modified heart valves having coatings comprising fatty acid or hyaluronic acid Z groups showed less thrombus accumulation and calcium deposition than observed for unmodified heart valves. Also, it was observed that significant calcium deposition only occurred at locations where thrombus accumulation occurred, which suggests that calcium deposition is generally dependent on thrombus accumulation.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of Silicone Rubber Valves

Heart valves comprising silicone rubber and a coating according to the present invention were prepared by dip casting.

The materials used in fabrication were high purity nitrogen gas, compressed oxygen gas, silicone rubber, Ivory soap (Proctor and Gamble, Cincinnati, Ohio), isopropanol, Isoplast 202 (Dow Chemical, Midland, Mich.), and 1,1,1-trichloroethane (TCE).

A. Solution Preparation: A 10% (w/w) solution of silicone rubber (HP100, Dow Corning) in TCE was prepared. Also, 200 mL of a 12 w/w % solution of silicone rubber in TCE and 200 mL of a releasing agent (3 w/v % of soap/water solution) were prepared.

B. Stent Preparation: A hard polymer stent machined from Isoplast 202 rod stock was washed in isopropanol using an ultrasonic water bath. Using forceps, the stent was placed in an oxygen plasma chamber and plasma etched for 1 hr. The stent was then removed from the plasma chamber and immediately submerged in the 10% silicone rubber/TCE solution for 10 min. This dip is intended to minimize contamination of the stent material. The stent was then removed and excess solution allowed to run off.

C. Stent Dip Casting: The prepared stent was placed in a 3-prong plastic valve stent holder, the holder attaching along the annulus of the stent so that stent tips were dipped first. The stent was then dipped into the 12% silicone rubber/TCE solution to the base of the stent tips a sufficient number of times to create a dip cast silicone rubber coated stent that fit snugly over a leaflet mandrel of a predetermined diameter. After each dip, the stent was allowed to rotate dry under nitrogen. Typically, the stent was dipped seven times, although dip number varied based on stent width and solution concentration changes due to evaporation.

D. Valve Dip Casting: All aluminum surfaces of a leaflet mandrel were first cleaned using water or isopropanol and a non-abrasive cloth or towel. The leaflet mandrel was dip coated by hand in 3% (w/v) Ivory soap solution (releasing agent) and allowed to rotate under dry nitrogen for at least 30 min. The dip cast silicone rubber coated stent was then placed over the leaflet mandrel and dipped into the 12% silicone rubber/TCE solution a number of times to produce leaflets of a desired thickness, typically 6–7 dips. Between each dip, the mandrel was rotated dry under dry nitrogen. After the last dip, both the stent and the mandrel were allowed to dry for 1 hr. The valve was cured for 4 hr at 177° C., and water was applied to remove excess releasing agent.

EXAMPLE 2

Surface Modification of Silicone Rubber and PEU Valves

This example shows the surface modification of polymer valve leaflets. Substrate polymers used were high performance silicone rubber (HP-100, Dow Corning) and epoxy-bisphosphonate-modified poly(ether urethane) (F2000-HEDP) (made by Dr. Robert J. Levy, University of Michigan, Ann Arbor, Mich.).

A. Coating leaflets with photoreactive fatty acid (Photo FA-1): The prototype polymer valves described in Example 1 were constructed using leaflets fabricated of either the above silicone rubber or, using the general procedure described in Example 1, epoxy-bisphosphonate-modified PEU test polymers. (The procedure for epoxy-bisphosphonate-modified PEU differed in using a solution of 10% polysiliconeurethane (PSU) (X7-4074, Dow Corning)/tetrahydrofuran (THF) solution instead of 10% silicone rubber/TCE solution in step B). Photo FA-1 (comprising a tetramer of ethylene oxide as the linking group Y) (Compound VI, SurModics Reagent #2040) was dissolved at a concentration of 5.0 mg/mL in isopropanol. After 5 min Ar plasma treatment, the valves were dipped into the photo FA-1 solution for 1 min at room temperature, slowly withdrawn from solution, dried in 20%-humidity air, and illuminated 3 min at 2 mW/cm$^2$ intensity within the 335–345 nm range using dual Dymax model PC-2 light sources (peak intensity 365 nm). The procedure was repeated to obtain 2× modified substrates.

B. Coating leaflets with photoreactive polyvinylpyrrolidone (Photo PVP): Prototype polymer valves as described in Example 1 were constructed using leaflets fabricated of silicone rubber. Photo PVP (SurModics Product Code PV05) was dissolved to a concentration of 5.0 mg/mL in water. After 5 min Ar plasma treatment, the valves were dipped into the photo PVP solution for 1 min at room temperature, slowly withdrawn from solution, dried in 20%-humidity air, and illuminated 3 min at 2 mW/cm2 intensity within the 335–345 nm range using dual Dymax model PC-2 light sources (peak intensity 365 nm). The procedure was repeated to obtain 2× modified substrates. The same procedure can be used to coat epoxy-bisphosphonate-modified PEU leaflets with PVP.

C. Coating leaflets with photoreactive hyaluronic acid (Photo HA-1): Prototype polymer valves were constructed as described in Examples 1 and 2B, using leaflets fabricated of epoxy-bisphosphonate-modified PEU or silicone rubber, respectively. Photo HA-1 (SurModics Reagent #28) was dissolved to a concentration of 10.0 mg/mL in 20% v/v isopropanol in water. Silicone rubber valves coated with photo PVP solution as described in Example 2B or epoxy-bisphosphonate-modified PEU valves fabricated following the general procedure of Example 1 were dipped into the photo HA-1 solution for 1 min at room temperature, slowly withdrawn from solution, dried in 20%-humidity air, and illuminated 4 min at 2 mW/cm$^2$ intensity within the 335–345 nm range using dual Dymax model PC-2 light sources (peak intensity 365 nm). The procedure was repeated to obtain 2× modified substrates.

EXAMPLE 3

Surface Modification of Silicone Rubber Valves with Fatty Acid, Polyvinylpyrrolidone, or Hyaluronic Acid For this Example, the substrate polymer used was a high performance silicone rubber HP-100 as described above. The photoreactive agents used were a photoreactive fatty acid (Compound II, Photo FA-2, SurModics Reagent #2041), photoreactive polyvinylpyrrolidone (Photo PVP, SurModics Product Code PV05), and Photo HA-2 (SurModics Reagent #24) as described above.

A. Coating silicone rubber leaflets with photo FA-2: The photo FA-2 modification procedure was identical to that used in reference to photo FA-1, Example 2, except the photo FA-2 solution was heated to 55° C. prior to incubation.

B. Coating silicone rubber leaflets with photo PVP: The photo PVP reagent described in Example 2 was dissolved to a concentration of 3.0 mg/mL in water. After 5 min Ar plasma treatment, valves were immersed, stent posts up, in the solution, illuminated 45 sec, then placed with stent posts down in a second batch of the solution. The valve was again illuminated 45 sec, rinsed in water, then illuminated 2 min wet-to-dry while rotating between dual lamps.

In one group of valves, after initial photo PVP treatment, valves were immersed in an isopropanol solution of tetrakis (4-benzoylbenzyloxymethyl) methane (as a photoprimer) (SurModics) and photo PVP (0.15/10 mg/mL), withdrawn from the solution at a rate of 0.05 cm/s, dried in 20%-humidity air, humidified, illuminated 2 min, rotated, illuminated 1 min, rotated, and illuminated 30 sec.

In another group of valves, after initial photo PVP treatment, valves were immersed in a solution of photoreactive hyaluronic acid different from that of Example 2 (Photo HA-2) at a concentration of 2.5 mg/mL in 50 v/v % isopropanol/water. Each valve was immersed stent posts up, withdrawn from the solution at a rate of 0.05 cm/s, dried in 20%-humidity air, humidified, illuminated 2 min, rotated, illuminated 1 min, rotated, and illuminated 30 sec. The valve was then immersed in the photo HA-2 solution with stent posts down, withdrawn at 0.01 cm/s, dried in 20%-humidity air, humidified, illuminated 2 min, rotated, illuminated 1 min, rotated, and illuminated 30 sec. The latter was twice repeated to obtain 3× modified substrates. The same procedure can be used to coat epoxy-bisphosphonate-modified PEU leaflets with photo HA-2, with or without initial photo PVP treatment.

EXAMPLE 4
In Vitro Mineralization Tests of Coated and Uncoated Polymer Samples This example illustrates the simulation of the in vivo mineralization of elastomeric materials under conditions of equivalent dynamic stress. The polymers used were (a) a polyetherurethane coated with a polysiliconeurethane (F2000 PEU/X7-4074 PSU); (b) epoxy-bisphosphonate-modified polyetherurethane F2000-HEDP (1.0 mg HEDP per 1.0 g polyetherurethane); (c) polyetherurethane urea (PEUU) (Biomer); and (d) high performance silicone rubber (SR) (HP 100). Samples of the polymeric materials were die cut from solvent cast films. Test samples were cyclically stressed in vitro in either calcium- and phosphorous-supplemented bovine plasma, or metastable calcium phosphate solution.

After removal from the test units, samples were rinsed, then inspected visually and by Fourier transform infrared spectroscopy (FTIR) using attenuated total reflectance (ATR) mode. Elemental analysis was performed by inductively coupled plasma (ICP)/atomic emission spectroscopy (AES). Molecular weight distribution of PU samples was obtained by gel permeation chromatography (GPC). Each specimen was blown dry with warm air. Dryness was verified by inspection of the FTIR spectra in areas where water appeared. An internal reflection element of germanium at an incident angle of 45°, open aperture, 4.0 resolution, and 16/sample scanning were used.

A. Plasma Incubation: Over a period of 8 wk, tensile bar samples were strained at 120 cycles per minute to yield a peak stress of 38 psi in heparinized (10,000 IU/L) bovine plasma supplemented with potassium phosphate and calcium chloride (final concentrations, 3.68 mM Ca, 2.84 mM phosphate, such that $([Ca^{+2}] \times [PO4^{-3}])=130$ mg/dL, assuming that native plasma contains 2.5 mM Ca and 0.67 mM phosphate). Little mineralization was evident after 8 wk incubation with plasma. Therefore, samples were stressed to 38 psi an additional 2 wk (for a total of 10 wk). Little mineralization of SR and PEU/PSU samples was evident after 10 wk, and therefore samples were stressed to 75 psi for an additional 2 wk. Samples were removed from the testers and adherent material was removed from the surface by 24 hr incubation with 0.6% w/w pepsin at 37° C., pH 1.8. Upon removal from the pepsin solution, each specimen was water rinsed, air dried, and weighed. Polymer samples were also similarly digested.

B. Calcium Phosphate Incubation: Over a period of 8 wk, tensile bar samples were strained at 120 cycles per minute to yield a peak stress of 38 psi in metastable calcium phosphate solution (potassium phosphate and calcium chloride [3.87 mM Ca, 2.32 mM phosphate], ampicillin [100 µg/mL], gentamicin [50 µg/mL], pH 7.4), then to 75 psi for an additional 2 wk. Adherent material was removed from the surface by 5 min agitation in 5% v/v nitric acid solution at room temperature. Each sample was air dried and weighed to ±0.0001 g. Each polyetherurethane specimen was digested in 2.5 mL concentrated nitric acid at 210W microwave power. The silicone rubber samples were digested similarly in two steps. Samples were first microwaved in a mixture of 1 mL concentrated hydrofluoric acid/1 mL concentrated sulfuric acid, then again after addition of 3 mL nitric acid.

Samples were also analyzed by GPC for changes in MW distribution. Samples were dissolved to 1 w/v % in dimethylacetamide (DMAC). Solutions were filtered through a 0.45 mm syringe filter. Thereafter, 200 mL dissolved polymer samples were fractionated serially through two Shodex columns ($10^3$, $10^4$). The column temperature was maintained at 80° C.

C. Visual observation of samples incubated with plasma: After 10 wk, the right front and left rear samples were removed from the test units (each of which holds four samples). Little deposit was present on any of the samples, but more deposit was visible on PEUU (Biomer) than on the epoxy-bisphosphonate-modified polyetherurethane (F2000-HEDP), the PSU-coated PEU (F2000/X7-4074), or the silicone rubber (HP100).

After an additional 2 wk incubation of the samples in plasma at higher cyclic stress (75 psi), the remaining samples were removed from the units. As shown in FIGS. 1–4, more deposit was present on PEUU (Biomer) and epoxy-bisphosphonate-modified PEU (F2000-HEDP) samples than on PSU-coated PEU (F2000/X7-4074) or silicone rubber (HP100) samples. Less deposit was observed in the high stress center than in the low stress ends of the HP-100 samples. In general, deposits were tightly adherent and rigid in the center of the sample.

FTIR spectra of the material adherent to samples stressed in plasma were similar to that of beta-tricalcium phosphate, an hydroxyapatite precursor. Strong phosphate peaks at 1030 $cm^{-1}$ suggest the presence of immature hydroxyapatite-like crystals, and characteristic peaks at 1530 $cm^{-1}$ and 1650 $cm^{-1}$ suggest the presence of protein in the matrix.

D. FTIR analysis of polymeric samples after removal of mineral deposits: FTIR spectra of polymers stressed in plasma analyzed after removal of mineral deposits provided no evidence for bulk chemical degradation of either silicone rubber (HP100), PSU-coated PEU (F2000/X7-4074), or epoxy-bisphosphonate-modified PEU (F2000-HEDP). In contrast, spectra of PEUU (Biomer) samples showed decreased intensity relative to controls of the peak at 1109 $cm^{-1}$ (indicative of soft segment ether), suggesting degradation of polymer soft segment. Further, a new peak was evident at 1632 $cm^{-1}$, suggesting increased urea carbonyl functionality. No new peak at 1174 $cm^{-1}$ (indicative of ester functionality) appeared in the Biomer spectra. In contrast, such a new peak appeared in the spectrum of a similar polyetherurethane (PEU) implanted, stressed, and caged subcutaneously in rats (for model description, see Marchant, R. et al., *J. Biomed. Mater. Res.* 17: 301–325 (1983)), reflecting the difference between in vitro and in vivo environments. However, both in vitro and in vivo studies demonstrated the instability of the PEU soft segment, which demonstrates that stress of unmodified polyurethane in plasma can effect changes in the bulk chemistry of the polymer.

E. Elemental analysis of mineral adherent to polymeric samples: Calcium and phosphorus content of the mineral adherent to the polymers was measured by ICP/AES. An attempt was made to differentiate between internal and external mineralization by analyzing both the mineral-lipid-protein layer and the polymers themselves. The adherent layer was first dissolved from the polymer by incubation in acidic enzyme solution, then analyzed for solubilized mineral indicative of external mineralization. The polymer was then dissolved in an acid solution, which was then analyzed for solubilized mineral to determine the amount of internal mineralization.

It was observed that less mineral was adherent to silicone rubber (HP-100) than to the other polymers stressed up to 12 wk in plasma. Polymer mineralization appeared to be an interfacial phenomenon. The deposits appeared to be nucleated immediately subsurface or appeared to grow from the interface into the polymer. These results demonstrate the causal relationship between polymer stress and polymer mineralization.

EXAMPLE 5
In Vivo Performance of Fatty Acid- and Hyaluronic Acid-Coated Valves Twelve valves prepared according to the present invention, having leaflets of high performance silicone rubber, surface modified with either tritiated or non-radioactive derivatives of either fatty acid or hyaluronic acid (photo FA-2 or photo HA-1 or -2, respectively) coatings, were implanted in the mitral position of sheep. One sample group consisted of 6 valves surface modified with hyaluronic acid, and the other sample group consisted of 3 valves surface modified with fatty acid. The techniques used for this implant study followed E. D. Irwin et al., "Long term evaluation of prosthetic mitral valves in sheep," *J. Invest. Surgery*, 6, 133–141 (1993). Briefly, juvenile sheep (30–35 kg to insure good valve size fit) were selected. The native mitral valve was excised and replaced with a heart valve of the present invention or a control. The valves were retrieved at about 150 days after implantation, and the explants were fixed in 10% neutral buffered formalin, and evaluated histopathologically.

Valves from each sample group were successfully retrieved after a nominal 150 day implant. Photo HA-1 and photo HA-2 valves successfully retrieved from animals after 150 day implant were designated POLY52 and POLY53; and JFV-61, JFV-62, and JFV-64, respectively; photo FA-2 valves successfully retrieved from animals after 150 day implant were designated POLY56, POLY57, JFV66, JFV67, and JFV69. The retrieved valves were compared with control valves having unmodified leaflets of high performance silicone rubber (designated as POLY30-POLY32). Upon gross examination, it was generally observed that thrombus accumulation and visible calcification on and in the surface modified valve leaflets were less than that observed on the unmodified valves, as shown in FIGS. 5–7.

As shown in the Figures, small thrombi were observed in the commissures, and red, thrombus-like adhesions were observed at the outflow cuff-stent interface of most valves. These thrombi are believed to be related to valve design. Further, paravalvular leaks (due to improper seating of the valve) were noted. Generally, collagen encapsulated the sewing cuffs of the valves, and no intrinsic calcific deposits and very little thrombus-like material was adherent to inflow and outflow aspects of the leaflets relative to non-surface-treated control valves. The results of these and other animal studies show that the modification of both silicone rubber and polyetherurethane with either hyaluronic acid or fatty acid decreased thrombus adhesion relative to the respective unmodified substrates.

EXAMPLE 6
Histopathology of Explanted Fatty Acid- and Hyaluronic Acid-Coated Valves Some valves were examined histopathologically to determine the extent of thrombosis and healing. In order to perform valve histopathology, a leaflet and a sewing cuff section from some of the explanted valves of Example 5 were embedded in glycol methacrylate or paraffin. Sections were stained with hematoxylin and eosin (HE) for cellular detail and morphology, with Masson's trichrome (TRI) for collagen, with phosphotungstic acid and hematoxylin (PA-HE) for fibrin, and using the von Kossa (VK) for calcified mineral. Histopathology of valves surface modified with hyaluronic acid (i.e., POLY52 and POLY53) confirmed that the sewing cuff was well healed, and showed no organizing thrombus adherent to valve leaflets. Histopathology of valves surface modified with fatty acid (i.e., JFV66, JFV67, and JFV69) also showed not only that the sewing cuffs were well healed, but also that the leaflets were free of thrombus.

EXAMPLE 7
Retention of Fatty Acid and Hyaluronic Acid Coatings in Explanted Valves To determine photoreagent retention by the surface modified valves, a second leaflet and sewing cuff section of some of the explanted valves of Example 5, i.e., those coated with tritiated fatty acid or tritiated hyaluronic acid, were incubated with 0.5 mL Soluene 350 solubilizing agent (catalog no. 6003038, Packard Instrument, Downers Grove, Ill.) at 55° C. for 1.5 hr, then 5.0 mL Hionic-Flour liquid scintillant (Packard Instrument). The radioactivity retained by each leaflet and sewing cuff was measured using the tritium window of a beta radiation counter. The reagent retentions of the leaflets after 5 month ovine mitral implant for the hyaluronic acid- and fatty acid-modified valves were 27.8% and 13.8%, respectively.

EXAMPLE 8
Mineralization of Explanted Fatty Acid- and Hyaluronic Acid-Coated Valves To quantify mineralization, another leaflet and sewing cuff section was removed from some of the explanted valves of Example 5, and intrinsic calcium and phosphorus content measured using ICP/AA. These results were compared with the calcium contents of (1) a five month implant of a bioprosthetic valve (Hancock Porcine Valve, Medtronic, Minneapolis, Minn.) (276 $\mu$g Ca/mg dry tissue) and (2) a five month implant of unmodified high performance silicone rubber valve prosthesis (1.7 $\mu$g Ca/mg dry tissue). The results showed that the intrinsic calcium content of the surface modified valve leaflets (both hyaluronic acid- and fatty acid-modified) was lower than that of unmodified bioprosthetic control, and not statistically different than the unmodified silicone rubber control. These results show that surface modification did not negatively affect intrinsic leaflet mineralization.

All of the compositions, methods, and apparatus disclosed and claimed herein can be made and executed without undue experimentation in light of the present disclosure. While the compositions, methods, and apparatus of this invention have been described in terms of preferred embodiments, it will be apparent to those of skill in the art that variations may be applied to the compositions, methods, and apparatus and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A biocompatible heart valve comprising:
   a stent defining a blood flow path; and
   a plurality of polymeric leaflets having a surface coating to provide resistance to in vivo pathologic thrombus formation and in vivo pathologic mineralization, wherein the surface coating comprises a precursor of the formula:

X—Y—Z wherein X is a chemically reactive group capable, upon activation, of bonding to the surface of the heart valve; Y comprises a compound selected from the group consisting of a $C_1$–$C_{10}$ alkyldiol; a $C_1$–$C_{10}$ diamine; a polyethyleneoxide (PEO); an amino-substituted PEO (MW=200–1450); a diamine-terminated PEO (MW=200–1450); ε-amino caproic acid (EAC); ethylene diamine (ED); diaminopropane (DAP), and derivatives of the foregoing; and Z is a fatty acid moiety, a hyaluronic acid moiety, a polyoxyethylene moiety, or a vinylpyrrolidone moiety.

2. A biocompatible heart valve comprising:
   a stent defining a blood flow path; and
   a plurality of polymeric leaflets having a surface coating to provide resistance to in vivo pathologic thrombus formation and in vivo pathologic mineralization, wherein the surface coating comprises a precursor of the formula:

X—Y—Z wherein X is selected from the group consisting of a substituted benzyl benzoyl having structure I:

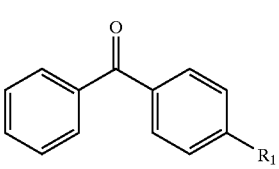

(I)

wherein R1 is a carboxyl group, and derivatives thereof;
   Y comprises diaminopropane (DAP), a diamine-terminated amide, and derivatives of diaminopropane and diamine-terminated amides; and, to provide resistance to in vivo pathologic thrombus formation and in vivo pathologic mineralization, wherein the surface coating comprises a precursor selected from the group consisting of:

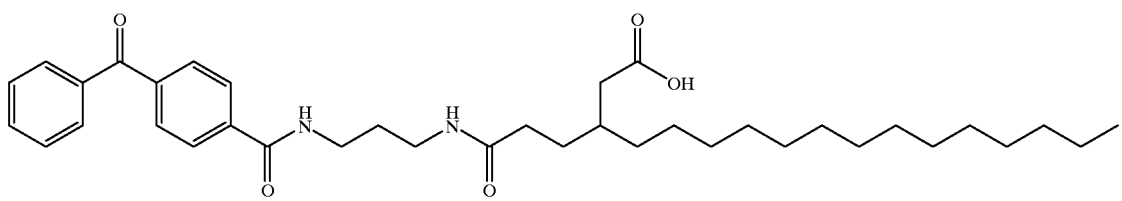

(II)

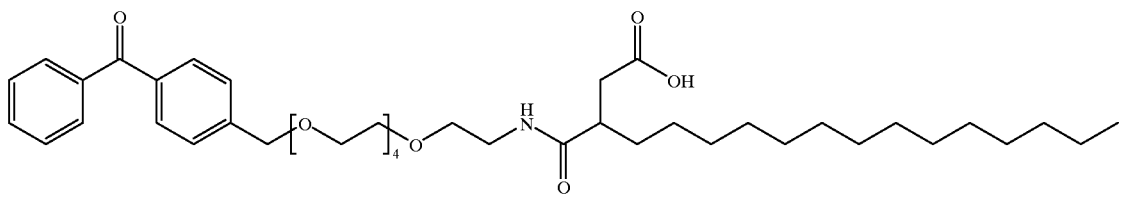

(III)

and derivatives of (II) and (III).

UNITED STATES PATENT AND TRADEMARK OFFICE
CERTIFICATE OF CORRECTION

PATENT NO. : 6,764,509 B2
DATED : July 20, 2004
INVENTOR(S) : Joseph Andrew Chinn, Jack R. Frautschi and Richard E. Phillips, Jr.

It is certified that error appears in the above-identified patent and that said Letters Patent is hereby corrected as shown below:

<u>Column 18,</u>
Line 21, after "amides; and," insert the following as a new paragraph:

-- Z is derived from a compound selected from functionalized fatty acids, functionalized hyaluronic acid, functionalized polyoxyethylene, functionalized heparin, or functionalized vinylpyrrolidone. --
Line 21, before "to provide" insert claim 3 as follows:

-- 3. A biocompatible heart valve comprising:

a stent defining a blood flow path; and a plurality of polymeric leaflets having a surface coating --

Signed and Sealed this

Nineteenth Day of October, 2004

JON W. DUDAS
*Director of the United States Patent and Trademark Office*